United States Patent [19]

Callens et al.

[11] Patent Number: 4,954,616

[45] Date of Patent: * Sep. 4, 1990

[54] USE OF GUANIDINE-RELATED COMPOUNDS COMPRISING A SUBSTITUTED TETRAPHENYLBORATE ION IN SOLUTION PHASE PIPTIDE SYNTHESIS

[75] Inventors: Roland Callens, Gent-Drongen; André Collin, Ligny, both of, Belgium

[73] Assignee: Solvay & Cie (Société Anonyme), Brussels, Belgium

[*] Notice: The portion of the term of this patent subsequent to May 8, 2007 has been disclaimed.

[21] Appl. No.: 207,877

[22] Filed: Jun. 17, 1988

[30] Foreign Application Priority Data

Jun. 19, 1987 [FR] France .................................. 87 08696

[51] Int. Cl.⁵ .............................................. C07K 1/02
[52] U.S. Cl. ................................... 530/333; 530/335; 530/338
[58] Field of Search ........................ 530/333, 335, 338

[56] References Cited

PUBLICATIONS

Chemical Abstracts, vol. 95, No. 4, Jul. 27, 1981.

*Primary Examiner*—Howard E. Schain
*Assistant Examiner*—Susan M. Perkins
*Attorney, Agent, or Firm*—Spencer & Frank

[57] ABSTRACT

Use of a guanidine-related compound in solution phase peptide synthesis, the guanidine-related compound including a tetraphenylborate ion and having the general formula:

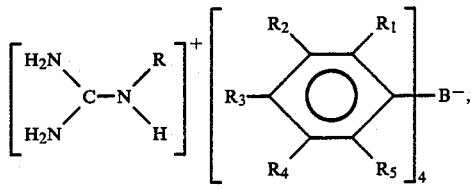

wherein R denotes an organic radical including at least one amine group, and $R_1$, $R_2$, $R_3$, $R_4$ and $R_5$ denote inorganic or organic groups independently of each other.

4 Claims, No Drawings

USE OF GUANIDINE-RELATED COMPOUNDS COMPRISING A SUBSTITUTED TETRAPHENYLBORATE ION IN SOLUTION PHASE PEPTIDE SYNTHESIS

CROSS-REFERENCE TO RELATED APPLICATION

This application is related to copending application No. 07/207,876 filed June 17th, 1988.

BACKGROUND OF THE INVENTION

1. Field of the Invention

The present invention relates to guanidine-related compounds comprising a substituted tetraphenylborate ion associated with a product comprising a guanidine-related group, and to a process for obtaining such compounds, which may be employed as a means for dissolving the product in which the protection of the guanidine-related group is insured, particularly in peptide synthesis from amino acids or peptides.

2. Description of the Related Art

German patent application DOS No. 2,716,477 discloses particularly N,N',N"-substituted guanidine salts of general formula:

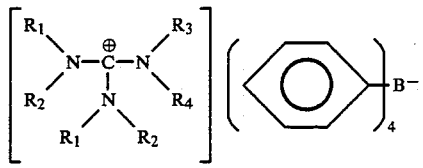

in which $R_1$, $R_2$, $R_3$ and $R_4$ denote an aliphatic, cyclic, arylated aliphatic, aromatic or heterocyclic radical and in which only $R_1$ may be a hydrogen atom.

These compounds, protonated on the carbon atom of the substituted guanidine-related group, are synthesized from a halogenated derivative of carbamic acid and from substituted thiourea and may be employed as catalysts, plant-protection agents and pharmaceutical dyes.

Furthermore, salts consisting of the tetrakis[3,5-bis(-trifluoromethyl)phenyl]borate anion and certain diazonium cations such as $ArN_2^+$ and $ArNHR_2^+$ in which Ar denotes an aryl radical and R a methyl radical, are also known (Bulletin Chem. Soc. Japan, 56, 796–801, 1983, vol. 56, N.3).

SUMMARY OF THE INVENTION

A new category of compounds has now been found, whose structural formula is related to that of the above-mentioned products, but in which all the valencies of the nitrogen atoms of the guanidine group save for one are saturated by hydrogen atoms.

More particularly, the compounds according to the invention comprise a guanidine-related group and a tetraphenylborate ion and correspond to the general formula:

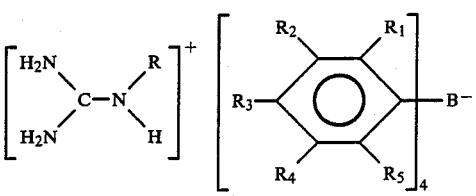

in which R denotes an organic radical comprising at least one other amine group and $R_1$, $R_2$, $R_3$, $R_4$ and $R_5$ denote inorganic or organic groups, independently of each other. R generally denotes a radical comprising, in addition to an amine group, a carboxylic group, it being possible for these groups to be optionally substituted.

Usually:

R denotes a radical of general formula:

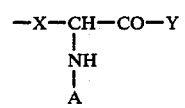

in which X, A and Y independently of each other denote linear, branched or cyclic, substituted or unsubstituted, saturated or unsaturated aliphatic radicals, aromatic radicals, arylated aliphatic radicals or heterocyclic radicals. A may also denote a hydrogen atom and Y a hydroxyl group or a halogen atom;

$R_1$, $R_2$, $R_3$, $R_4$ and $R_5$ denote monovalent inorganic groups chosen from hydrogen, the hydroxyl group and the halogens such as chlorine and fluorine; or organic groups consisting of aliphatic radicals, of arylated aliphatic radicals and of aromatic radicals, including heterocyclic aromatic radicals, it being possible for all these radicals to comprise linear, branched or cyclic, saturated or unsaturated entities, as well as heteroatoms.

Generally,

X denotes a linear, branched or cyclic, substituted or unsubstituted, saturated or unsaturated aliphatic radical containing up to 25 carbon atoms;

A denotes a hydrogen atom, an aliphatic or aromatic radical comprising heteroatoms or otherwise, such as protecting groups or activating groups, one or more amino acids linked by peptide bonds, in which groups are optionally substituted by protecting groups or activating groups;

Y denotes a hydroxyl group, a halogen atom, an aliphatic or aromatic radical optionally comprising heteroatoms, such as protecting groups or activating groups, an amino group, an amino acid or a peptide in which certain groups are optionally substituted by protecting groups or activating groups as well as amino groups of general formula $NR_6R_7$ in which $R_6$ and $R_7$ independently of each other denote a hydrogen atom or an alkyl group containing from 1 to 3 carbon atoms;

$R_1$, $R_2$, $R_3$, $R_4$ and $R_5$ denote a hydrogen atom or an organic group chosen from alkyl, alkoxyalkenyl or alkenyl radicals containing from 1 to 10 carbon atoms and optionally containing heteroatoms.

Preferably:

X denotes an alkyl radical of general formula $(CH_2)_n$ in which n is an integer between 1 and 10;

A denotes a hydrogen atom, an amino acid, a peptide or a protecting group;

Y denotes a hydroxyl group, a protecting group, an activating group, an amino acid or a peptide, $R_1$, $R_2$, $R_3$, $R_4$ and $R_5$ denote a hydrogen atom or an alkyl radical containing from 1 to 5 carbon atoms and optionally comprising heteroatoms such as halogen atoms, especially chlorine and fluorine.

In a very particularly preferred manner:

X denotes the radical $(CH_2)_n$ in which n is between 1 and 6;

A denotes a hydrogen atom, a protecting group such as especially the benzyloxycarbonyl (Z) or tert-butyloxycarbonyl (t-Boc) groups, an amino acid or a peptide optionally substituted by these same protecting groups;

Y denotes a hydroxyl group, a protecting group such as a benzyl ester, an activating group such as N-hydroxylsuccinimide, an amino acid or a peptide optionally substituted with protecting and/or activating groups or an amino group;

$R_1$, $R_2$, $R_3$, $R_4$ and $R_5$ independently of each other denote a hydrogen atom or an alkyl radical containing from 1 to 3 carbon atoms and heteroatoms such as chlorine or fluorine.

Lastly, good results have been obtained when:

X denotes the radical $(CH_2)_3$;

A denotes a hydrogen atom, an optionally substituted amino acid or a protecting group such as benzyloxycarbonyl or tert-butyloxycarbonyl, and Y a hydroxyl group or an optionally substituted amino acid, $R_1$, $R_3$ and $R_5$ denote a hydrogen atom and $R_2$ and $R_4$ a substituted methyl group such as the trifluoromethyl group.

An amino acid is understood to mean any organic acid containing at least one carboxylic group and at least one primary or secondary amine group, such as the known natural amino acids or synthetic amino acids. Peptide is understood to mean any peptide originating from any combination of natural or synthetic amino acids.

A protecting group is understood to mean any compounds mentioned for this purpose in the literature and more particularly by:

M. Bodanszky, Principles of Peptide Synthesis, 1984, Volume 16, Reactivity and Structure Concepts in Organic Chemistry, M. Bodanszky, A. Bodanszky, The Practice of Peptide Synthesis, 1984, Volume 21, Reactivity and Structure Concepts in Organic Chemistry.

By way of illustration, the following protecting groups may be employed in the compounds of the invention:

acyl-type protecting groups such as especially formyl, trifluoroacetyl, phthaloyl, 4-toluenesulphonyl, benzenesulphonyl, nitrophenylsulphenyl, and 2-nitrophenylsulphenyl, aromatic urethane-type protecting groups such as especially substituted or unsubstituted benzyloxycarbonyl such as p-chlorobenzyloxycarbonyl, p-nitrobenzyloxycarbonyl, p-bromobenzyloxycarbonyl, p-methoxybenzyloxycarbonyl, benzhydryloxycarbonyl, 2-(4-biphenylyl)propyl(2)oxycarbonyl, 2-(3,5-dimethyloxyphenyl)propyl(2)oxycarbonyl, and triphenylphosphonoethyloxycarbonyl, aliphatic urethane-type protecting groups such as especially tert-butyloxycarbonyl, diisopropylmethoxycarbonyl, isopropyloxycarbonyl, ethoxycarbonyl, allyloxycarbonyl, 9-fluorenylmethyloxycarbonyl, 2-methylsulphonylethyloxycarbonyl, and 2,2,2-trichloroethyloxycarbonyl, cycloalkyl urethane-type protecting groups such as especially cyclopentyloxycarbonyl, adamantyloxycarbonyl, cyclohexyloxycarbonyl, tert-amyloxycarbonyl and isobornyloxycarbonyl, thiourethane-type protecting groups such as especially phenylthiocarbonyl, alkyl-type protecting groups such as especially triphenylmethyl (trityl) and benzyl, trialkylsilane groups such as trimethylsilane, and alkoxy groups such as especially methyl ester, ethyl ester, tert-butyl ester and benzyl ester.

An activating group is intended to mean any known or unknown activating group such as those mentioned in the literature and more particularly in the papers by:

M. Bodanszky,

M. Bodanszky, A. Bodanszky, referred to earlier.

Usually, the activating group employed is, an oxycarbonyl, oxycarboxyl, N-oxyimidoyl, or imidazoyl group such as, especially, pivaloyloxycarbonyl, N-hydroxysuccinimidoyl, dicyclohexylcarbodiimidoyl and 4-nitrophenyl ester.

The preferred compounds according to the invention correspond to the formulae:

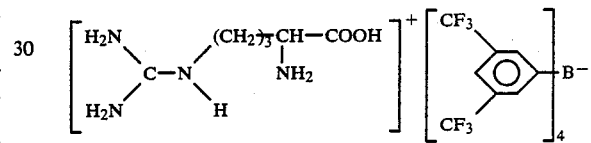

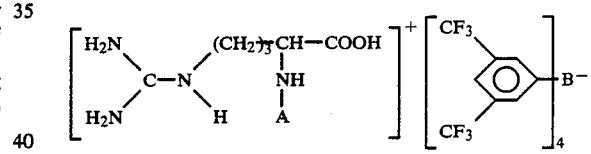

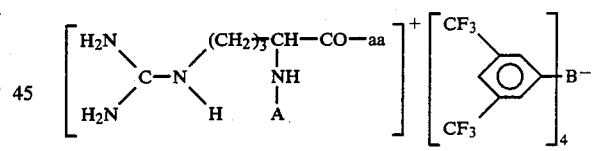

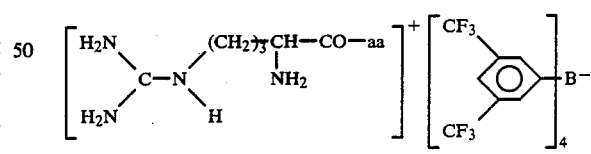

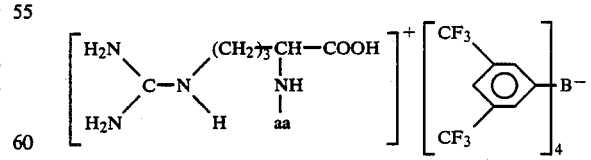

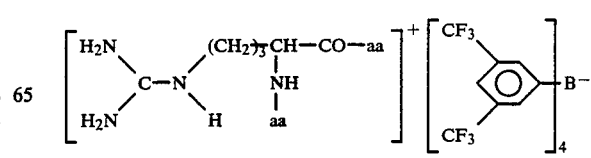

in which aa denotes an amino acid or a peptide linked via a peptide bond to arginine and in which the amine and carboxylic groups are optionally protected or substituted. A protection of this kind is made necessary when certain functional groups, in particular amine or carboxylic, must be blocked to avoid their being involved in subsequent reactions when the compound is used. The terminal carboxylic group of certain amino acids or peptides may, furthermore, be substituted by an amine group such as the -NH$_2$ or -NH-CH$_2$-CH$_3$ group.

In a particularly preferred manner, aa denotes an amino acid.

The compounds according to the invention may be prepared by any appropriate organic synthesis making use of known or unknown reactions and applying generally or particularly to a single determined compound or to a class of compounds.

A process which has given good results for the preparation of the compounds according to the invention consists in employing a substituted tetraphenylborate salt and a product comprising a guanidine group.

The substituted tetraphenylborate salts employed for the synthesis of the compounds according to the invention may be formed by starting with any inorganic or organic base.

More particularly, a nitrogenous organic base such as a secondary, tertiary or heterocyclic amine is employed as an organic base. Good results have been obtained with triethylamine, diisopropylethylamine, N-methylmorpholine, N-ethylmorpholine, N-methylpiperidine, N-ethylpiperidine, tri-n-butylamine, dicyclohexylamine and imidazole.

As an inorganic base, it is usual to employ an alkali or alkaline-earth metal hydroxide, preferably an alkali metal hydroxide such as especially sodium hydroxide or potassium hydroxide, and magnesium hydroxide.

A sodium substituted tetraphenylborate, such as sodium tetrakis [3,5-bis(trifluoromethyl)phenyl]borate is employed in a particularly preferred manner.

The substituted tetraphenylborate salt is used in the reaction in the presence of a solvent or of a mixture of solvents. Generally, a single polar organic solvent is employed such as, in particular, dimethyl sulphoxide (DMSO), N,N'-dimethylformamide (DMF), N-methylpyrrolidone, acetonitrile or a chlorinated solvent. Good results have been obtained with N,N-dimethylformamide, chloroform, dichloromethane and carbon tetrachloride.

The quantity of substituted tetraphenylborate salt employed may vary within wide limits. From 20 to 1 mole of substituted tetraphenylborate salt is generally employed per mole of product comprising the guanidine group. Preferably, from 10 to 1 mole of substituted tetraphenylborate salt is employed. In a particularly preferred manner, 1 mole of substituted tetraphenylborate salt is employed per mole of product comprising the guanidine group.

The other operating conditions employed in the process for preparing the compounds according to the invention are not critical for the invention. Thus, the pressure at which the process is carried out is generally between 0.1 and 10 bars and good results have been obtained at atmospheric pressure. The temperature at which the process is carried out is usually between −60° and 100° C. and may vary depending on the nature of the reactants and the compound which it is ultimately intended to prepare.

The process may be carried out in any apparatus designed for this purpose.

The compounds of the invention can be employed particularly as intermediates for chemical synthesis.

As a result of their solubility in organic solvents, they may be employed particularly when they themselves couple with other products; in particular in the synthesis of peptides from amino acids, particularly as described in European patent application No. 0,184,243, which relates to a process involving a trialkylcyanosilane.

Furthermore, the fact that the substituted tetraphenylborate ion is the counterion of the guanidine group, which it protects, makes it possible to ensure the protection of this guanidine group during the production of selective couplings and thus to obtain products with higher purity during the syntheses. In fact, at the end of the peptide synthesis, the substituted tetraphenylborate ion is easily displaced from the product containing the guanidine group by any known method, either by extraction in the form of a quaternary ammonium salt, or by precipitation in water in the form of an amine salt, and this makes it possible, on the one hand, to release the guanidine group and, on the other hand, to recover the substituted tetraphenylborate ion which can be recycled after an appropriate treatment.

More particularly, the invention relates to the use of the substituted tetraphenylborate ion as a means for solubilizing arginine and peptides containing unprotected arginines in the side chain, in organic solvents.

The compounds according to the invention, which are soluble in organic solvents, exhibit excellent stability in an organic medium. Arginine and peptides containing arginines can be extracted from their aqueous solution into an organic medium in the form of substituted tetraphenylborate. This property makes it easier to separate peptides by continuous extraction methods such as, in particular, the method known as CCD (counter-current distribution) which employs a water/organic medium two-phase extraction.

DESCRIPTION OF THE PREFERRED EMBODIMENTS

The examples which follow are used to illustrate the invention without, however, limiting its scope.

In these examples, the following abbreviations have been employed:

Arg : arginine
Gly : glycine
Leu : leucine
Pro : proline
O-Piv : pivaloyloxy (trimethylacetyloxy)
O-Succ: N-hydroxysuccinimide
Z : protecting group of the benzyloxycarbonyl type
Boc : protecting group of the tert-butyloxycarbonyl type
t-Boc : protecting group of the tert-butyloxycarbonyl type
DMF : N,N-dimethylformamide
Et : ethyl group -CH$_2$-CH$_3$
DCC : dicyclohexylcarbodiimide
ONb : 4-nitrobenzyl ester
HONb : N-hydroxy-5-norbornene-2,3-dicarboximide
HBr : hydrogen bromide
HOAc : acetic acid
Mbh : bis-para-methoxybenzhydryl
TFPB-Na : sodium tetrakis[3,5-bis(trifluoromethyl)phenyl]borate.

EXAMPLE 1

Synthesis of the compound formed by the tripeptide t-Boc-Leu-Arg-Pro and the tetrakis[3,5-bis(trifluoromethyl)phenyl]borate ion 112 g of water, 8.4 g (100 mmol) of NaHCO$_3$ and 8.66 g (20 mmol) of 2 HBr.Arg-Pro are introduced successively at ambient temperature into a 250-ml thermostated reactor fitted with a condenser and a stirring system.

After the mixture has completely dissolved and CO$_2$ has ceased to be evolved, 7.85 g (20 mmol) of t-Boc-Leu-ONb, dissolved in 80 g of dimethoxyethane, are added quickly.

After 15 hours' maturation with stirring at ambient temperature, the reaction solution is concentrated by evaporation at 40° C. under reduced pressure so as to give a residual solution of approximately 100 ml. This residue is adjusted to a pH of 2.5 by adding approximately 100 ml of 1N HCl solution. 200 ml of CH$_2$Cl$_2$ and 17.32 g (20 mmol) of TFPB-Na are then added. The mixture obtained is kept vigorously stirred at ambient temperature for 30 min and is then left to settle for 2 hours. The dense organic phase is drawn off and is then subjected to evaporation at 40° C. under reduced pressure.

The dry residue of 28.7 g is in the form of a powdery white solid and its t-Boc-Leu-Arg-Pro content is 29 % by weight, which represents a recovery of 17.2 mmol, i.e. a coupling efficiency of 86 %, whereas the efficiency is only 60 % if no tetrakis[3,5-bis(trifluoromethyl)phenyl]borate ion is employed. Examination of the aqueous phase shows that the extraction of the compound formed by the tetrakis[3,5-bis(trifluromethyl)phenyl]borate ion and the t-Boc-Leu-Arg-Pro tripeptide has been quantitative.

EXAMPLE 2

Use of the compound obtained in Example 1

1 mmol of the compound obtained in Example 1 is dissolved in 10 ml of 0.1 N HCl in a 250-ml thermostated reactor fitted with a condenser and a stirring system, and 10 ml of CH$_2$Cl$_2$ are then added After having stirred for 15 min, the organic phase is drawn off, is dried over MgSO$_4$, and is filtered. The filtrate and the washings (5 ml) are recovered directly in a 50-ml reactor which is fitted with a magnetic stirrer.

After 179 mg (1 mmol) of HONb have been added, the mixture is cooled to 0° C. and 206 mg (1 mmol) of DCC are added. The activation is allowed to continue for one hour at 0° C. and one hour at ambient temperature, and 301 mg (1 mmol) of Gly-Mbh are then added.

Stirring is continued for 15 hours. At this time, no precipitate has appeared To exhaust the HONb in the reaction mixture, the latter is washed twice with 20 ml of 5 % NaHCO$_3$. The dense phase is transferred using a syringe and is evaporated down under reduced pressure at 30° C.

On being taken up with Et$_2$O, the dicyclohexylurea precipitates. After filtration, the filtrate is concentrated and is dried under mechanical-pump vacuum (1 mm Hg).

The residue weighs 1.5 g, comprising the crude tetrapeptide (t-Boc-Leu-Arg-Pro-Gly-NH-Mbh) with a peptide purity of approximately 94 %, with an overall yield of 86%. The identity of the tetrapeptide is confirmed by NMR.

EXAMPLE 3

Synthesis of the compound formed by the tetrakis[3,5-bis(trifluoromethyl)phenyl]borate ion and the substituted peptide Leu-Arg-Pro-Gly-NH$_2$ 280 mg (0.5 mmol) of 2HOAc.Leu-Arg-Pro-Gly-NH$_2$ are dissolved in 5 ml of water. The α-amino group is released by adding 5 ml of 0.1N NaOH (pH=10.47). 443 mg of TFPB-Na are suspended in 10 ml of CH$_2$Cl$_2$ and the two solutions are mixed.

After stirring for 15 min, the dense phase is drawn off and is concentrated in a rotary evaporator.

Drying of the residue yields quantitatively the compound formed by the TFPB ion and the substituted tetrapeptide, ready for use.

The side chain of arginine remains protected by the TFPB ion, while the α-amino group is free, and this fragment can therefore be coupled with an amino acid or a peptide without a base being added.

What is claimed is:

1. Use of a guanidine-related compound in solution phase peptide synthesis, the guanidine-related compounds comprising a tetraphenylborate ion and having the general formula:

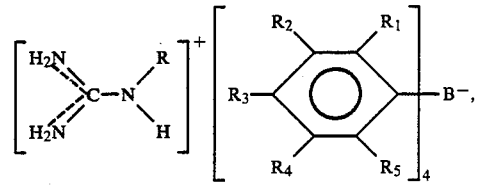

wherein R denotes an organic radical comprising at least one amine group, and $R_1$, $R_2$, $R_3$, $R_4$ and $R_5$ denote inorganic or organic groups independently of each other.

2. Use of a guanidine-related compound in solution phase peptide synthesis, the guanidine-related compound comprising a tetraphenylborate ion and having the general formula:

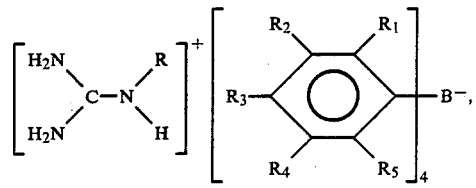

wherein R denotes an organic radical comprising at least one amine group and a carboxylic group, at least one of which at least one amine group and carboxylic group may be substituted, and wherein $R_1$, $R_2$, $R_3$, $R_4$ and $R_5$ denote inorganic or organic groups independently of each other.

3. Use of a guanidine-related compound in solution phase peptide synthesis, the guanidine related compound comprising a tetraphenylborate ion having the general formula:

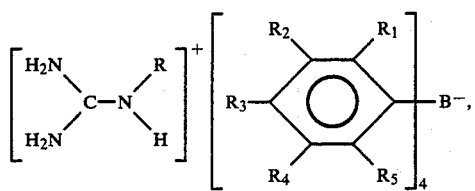

wherein R denotes an organic radical comprising at least one amine group and a carboxylic group, at least one of which at least one amine group and carboxylic group may be substituted, and having the general formula:

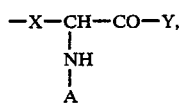

in which X, A and Y independently of each other denote linear, branched or cyclic, substituted or unsubstituted, saturated or unsaturated aliphatic radicals, aromatic radicals, arylated aliphatic radicals or heterocyclic radicals, and in which A may also denote hydrogen and Y may also denote a hydroxyl group or halogen, and wherein $R_1$, $R_2$, $R_3$, $R_4$ and $R_5$ each denote an inorganic or organic group independently of each other, the inorganic group being a monovalent inorganic group which is one of hydrogen, a hydroxyl group, and halogen, and the organic group consisting of an aliphatic radical, which aliphatic radical is one of an arylated aliphatic radical and an aromatic radical, including a heterocyclic aromatic radical, it being possible for all these radicals to comprise linear, branched or cyclic, saturated or unsaturated entities, as well as heteroatoms.

4. Use of a guanidine-related compound in solution phase peptide synthesis, the guanidine-related compound comprising a tetraphenylborate ion, having the general formula:

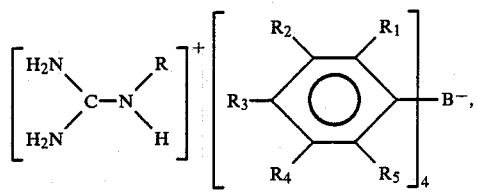

wherein R denotes an organic radical comprising at least one amine group and a carboxylic group, at least one of which at least one amine group and carboxylic group may be substituted, and having the general formula:

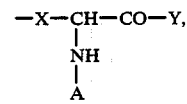

in which X, A and Y independently of each other denote linear, branched or cyclic, substituted or unsubstituted, saturated or unsaturated aliphatic radicals, aromatic radicals, arylated aliphatic radicals or heterocyclic radicals, and in which A may also denote hydrogen and Y may also denote a hydroxyl group or halogen, and wherein $R_1$, $R_2$, $R_3$, $R_4$ and $R_5$ each denote an inorganic or organic group independently of each other, the inorganic group being a monovalent inorganic group which is one of hydrogen, a hydroxyl group, and halogen, and the organic group consisting of an aliphatic radical, which aliphatic radical is one of an arylated aliphatic radical and an aromatic radical, including a heterocyclic aromatic radical, it being possible for all these radicals to comprise linear, branched or cyclic, saturated or unsaturated entities, as well as heteroatoms, and wherein X denotes a $-(CH_2)-_3$ radical, A denotes hydrogen, an optionally substituted amino acid or a protecting group such as a benzyloxy-carbonyl group or a tert-butyloxycarbonyl group, Y denotes a hydroxyl group or an optionally substituted amino acid, $R_1$, $R_3$ and $R_5$ denote hydrogen, and $R_2$ and $R_4$ denote a substituted methyl group such as the trifluoromethyl group.

* * * * *